US00PP33015P2

(12) United States Plant Patent
Walker et al.

(10) Patent No.: US PP33,015 P2
(45) Date of Patent: May 4, 2021

(54) GRAPEVINE PLANT NAMED 'CAMINANTE BLANC'

(50) Latin Name: ***Vitis vinifera* L.**
Varietal Denomination: Caminante Blanc

(71) Applicant: The Regents of the University of California, Oakland, CA (US)

(72) Inventors: Michael Andrew Walker, Davis, CA (US); Alan C. Tenscher, Davis, CA (US); Summaira Riaz, Davis, CA (US); Ninfa Romero, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/602,592

(22) Filed: Nov. 5, 2019

(51) Int. Cl.
*A01H 5/08* (2018.01)
*A01H 6/88* (2018.01)

(52) U.S. Cl.
USPC ..... Plt./205

(58) Field of Classification Search
USPC ..... Plt./205, 206
See application file for complete search history.

(56) References Cited

PUBLICATIONS

The Apr. 19, 2019 Test Agreement For Grapevines (No. 2019-5008) between Frog's Leap Winery and The Regents of the University of California, 6 pages.
The May 16, 2017 Test Agreement For Grapevines (No. 2017-5008) between Wonderful Nurseries, LLC and The Regents of the University of California, 7 pages.
The May 17, 2017 Test Agreement For Grapevines (No. 2017-5011) between Sunridge Nurseries, Inc. and The Regents of the University of California, 6 pages.
The May 18, 2017 Test Agreement For Grapevines (No. 2017-5009) between Novavine and The Regents of the University of California, 6 pages.
The May 24, 2017 Test Agreement For Grapevines (No. 2017-5010) between Sutter Home Winery, Inc. and The Regents of the University of California, 7 pages.

*Primary Examiner* — Susan McCormick Ewoldt
(74) *Attorney, Agent, or Firm* — McKee, Voorhees & Sease, PLC

(57) ABSTRACT

A new and distinct variety of grapevine plant named 'Caminante Blanc', particularly selected for its high resistance to Pierce's disease, as well as quality of fruit and wines produced is disclosed.

6 Drawing Sheets

Botanical classification: *Vitis vinifera* L.

Varietal denomination: The varietal denomination of the claimed variety of grapevine plant is 'Caminante Blanc'.

BACKGROUND OF THE INVENTION

Pierce's disease (PD) is common across the southern United States from Virginia to northern California. It is also common across Mexico and Central America. The disease is caused by the bacterium *Xylella fastidiosa*, which is hosted by a very wide range of native and ornamental plants. The bacterium is spread by xylem feeding insects as vectors, primarily sharpshooters. PD is one of the few diseases that rapidly kills wine, table, and raisin grape cultivars of the cultivated grape, *Vitis vinifera*. Vector populations can be limited with insecticides, but these are difficult to use near their typically riparian native habitat or in the ornamental landscapes in which they flourish. Breeding for PD resistance has been active for over 70 years, but progress has been very slow due to a poor understanding of the germplasm and the typically multigenic nature of the resistance in most of the resistant grape species. The two most commonly grown PD resistant varieties, 'Blanc du Bois' and 'Lenoir' ('Lenoir' is also known as 'Black Spanish' or 'Jacquet'), are $F_1$ hybrids between *V. vinifera* cultivars and resistant American grape species from the southern United States, and are therefore only about 50% of *V. vinifera*. 'Blanc du Bois' and 'Lenoir' produce wines with lower quality than *V. vinifera* wine grape varieties, and they are tolerant of, rather than resistant to, *X. fastidiosa* infection, which results in their potential to expand areas damaged by PD due to their ability to act as host plants for the bacteria and vectors.

Grapevine is an important and valuable crop. Accordingly, there is a need for new varieties of grapevine plant. In particular, there is a need for improved varieties of grapevine plant that produce high quality fruit for winemaking and are resistant to Pierce's disease.

SUMMARY OF THE INVENTION

In order to meet these needs, the present invention is directed to an improved variety of grapevine plant. In particular, the invention relates to a new and distinct variety of grapevine plant (*Vitis vinifera* L.), which has been denominated as 'Caminante Blanc'. Grapevine plant variety 'Caminante Blanc' possesses very strong resistance to the bacterial causal agent of Pierce's disease (PD), and produces very high quality fruit and wines therefrom that are indistinguishable from the widely grown European wine grape cultivars. Other PD resistant cultivars are known, but their fruit and winemaking quality are poor in comparison to 'Caminante Blanc' and their resistance is much lower.

In particular, grapevine plant variety 'Caminante Blanc' is a white wine grape selection that is about 97% *V. vinifera* (including 62.5% 'Cabernet Sauvignon', 12.5% 'Chardonnay', and 12.5% 'Carignane') and is highly resistant to PD as shown in repeated greenhouse evaluations. In comparison, the two most commonly grown PD resistant varieties, 'Blanc du Bois' and 'Lenoir', are only about 50% of *V. vinifera*. 'Caninante Blanc' has been planted in field trials in Davis and in Ojai, Calif. 'Caminante Blanc' has small berries and small compact clusters. It blooms relatively late, ripens mid-season, and has medium productivity. Wines made from fruit of 'Caminante Blanc' grown in Davis, Calif. may be described as: 'light straw-gold color', 'apple-melon', 'lychee', 'floral aromas', 'pineapple', 'green apple', 'juicy', 'harmonious', and 'well-balanced'.

Pedigree and Breeding History

The development of this new grapevine variety is in part a result of the discovery of a single dominant gene for resistance to *Xylella fastidiosa*, the bacterial causal agent of Pierce's disease (PD). The source of the PD resistance is a form of *V. arizonica* ('b43-17') that appears to have some candicans parentage and is from Monterrey, Mexico. 'b43-17' was crossed to the susceptible *V. rupestris* 'A. de Serres' to create the F8909 population, Neither 'b43-17' nor 'A. de Serres' are patented. The resistance from 'b43-17' was found to be inherited as a single dominant gene (locus), and this resistance gene, PdRl, was genetically mapped using the F8909 population by a grapevine breeding program. Tightly linked simple sequence repeat (SSR) markers were developed and were used in marker-assisted selection to exclude susceptible plants from evaluation in each round of selection. All the progeny with PdRl were tested for PD resistance and only those with strong resistance were considered for use as parents. Potential parents were also screened for fruit quality over generations and only those with good quality fruit and that appeared like *V. vinifera* were selected.

Line 'F8909-08' from the F8909 population was crossed to 'P79-101', a highly susceptible, advanced *V. vinifera* table grape selection from a grape breeding program. The resulting 'F8909-08' X 'P79-101' $F_1$ generation and progeny thereof were screened with the SSR markers for resistance to *X. fastidiosa* under greenhouse conditions. A highly resistant selection from the 'F8909-08' X 'P79-101' cross, '00504-20', was crossed to another *V. vinifera* table grape from a grape breeding program, 'B52-89', to create 'A81-138', which was also selected for its very high resistance to PD. 'A81-138' was then used to cross to *V. vinifera* wine grapes for several generations of modified backcrossing to obtain the candidate selection '09338-016', which was later named as 'Caminante Blanc'. These backcrosses were modified because of the high heterozygosity and recessive load found in grapes. Hence, to avoid exposure of deleterious recessive alleles, each generation of backcrossing was to a different and unrelated high quality *V. vinifera* cultivar.

Accordingly, the parentage of 'Caminante Blanc' is '07371-20' ('F2-35' ('Cabernet Sauvignon' X 'Carignane') X 'U0502-026' ('A81-138' X 'Chardonnay')) X 'Cabernet Sauvignon' to produce '09338-016'. 'Caminante Blanc' was particularly selected for its high resistance to Pierce's disease, as well as the quality of its fruit and wines produced therefrom. None of the parents across the multiple backcross generations are patented. '09338-016' has deeply lobed leaves with large irregular teeth on the leaf margin. 'Cabernet Sauvignon' is not only very susceptible to *X. fastidiosa* it has deeply lobed leaves, has lobes with small sinuses in them and has relatively short teeth on the leaf margin. 'Caminante Blanc' can be distinguished from its female parent '07371-20' in that 'Caminante Blanc' has perfect flowers whereas '07371-20' has pistillate flowers.

BRIEF DESCRIPTION OF THE DRAWINGS

This new grapevine plant variety is illustrated by the accompanying photographs. The colors shown are as true as can be reasonably obtained by conventional photographic procedures. The photographs are of plants that are five to seven years old. Colors referred to are in reference to The Royal Horticultural Society Colour Charts Edition V.

FIG. 1 shows simple sequence repeat (SSW) marker data establishing a DNA fingerprint for 'Caminante Blanc' with nine pure *Vitis vinifera* cultivars for comparison. Alleles for marker-assisted selection of the *Xylella fastidiosa* locus (PdRl) are shown in red.

DETAILED BOTANICAL DESCRIPTION

The following is a detailed description of the new grapevine plant variety designated as 'Caminante Blanc', including the key differentiating characteristics of this variety and comparisons of characteristics of 'Caminante Blanc' to other grapevine varieties. Unless otherwise indicated, evaluation data were taken from five- to seven-year-old plants, grown in Davis, Calif.

Classification:

*Family*.—Vitaceae.

*Botanical name*.—*Vitis vinifera* L.

*Common name*.—Grapevine.

*Variety name*.—'Caminante Blanc'.

Parentage:

*Female parent*.—'07371-20' (unpatented).

*Male parent*.—'Cabernet Sauvignon' (unpatented) Note that 'Cabernet Sauvignon' is a hermaphroditic cultivar and thus can be used as a maternal or paternal parent.

Plant:

*Berries*.—Small, golden-green, spherical, with thin whitish bloom.

*Clusters*.—Small to medium, compact, short conical to cylindrical often winged.

*Leaves*.—Five-lobed, round in outline, over lapping lateral sinuses, urn-shaped petiolar sinus with naked veins, distinctive large sharp teeth on leaf margin, lobes have extra sinus to make them five- to nine-lobed, red-purple petiole, glabrous leaves.

*Shoot tips*.—Red-bronze, with sparse tomentum.

*Production*.—Blooms relatively late, ripens mid-season, medium productivity

*Method of propagation*.—Vegetative propagation via woody or herbaceous cuttings, or budding and grafting to rootstock. 'Caminante Blanc' has been asexually reproduced in Davis, Calif. Any rootstock can be used with the variety. Most often it will be grown on rootstocks that resist grape phylloxera and or nematodes. In testing, selections were evaluated grafted on '1103P' rootstock which is not patented. It was chosen for ease of propagation and because it is widely used in CA. The variety has been grafted on many other rootstocks for testing in field trials as well.

'Caminante Blanc' has the highest form of resistance to *X. fastidiosa* coupled with the highest wine quality of any PD resistant wine grape yet produced. 'Caminante Blanc' is selected for very high resistance, not the more commonly found tolerance, to prevent the production of host plants capable of further spreading PD to surrounding vineyards.

'Caminante Blanc' has a very strong PD resistance and the highest wine quality of any currently used PD resistant wine grape. PD is one of the few diseases that kill susceptible grapevines. Two most popular PD resistant wine grape varieties, 'Blanc du Bois' and 'Lenoir' ('Lenoir' is also known as 'Black Spanish' or 'Jacquez'), were used as controls or standards in all testing so that the wine quality and resistance of the candidate variety could be compared to available PD resistant varieties used across the southern United States. It is noted that 'Blanc du Bois' and 'Lenoir' have relatively poor wine quality and are tolerant, not resistant, to PD. Neither 'Blanc du Bois' nor 'Lenoir' are patented.

Figure 2:
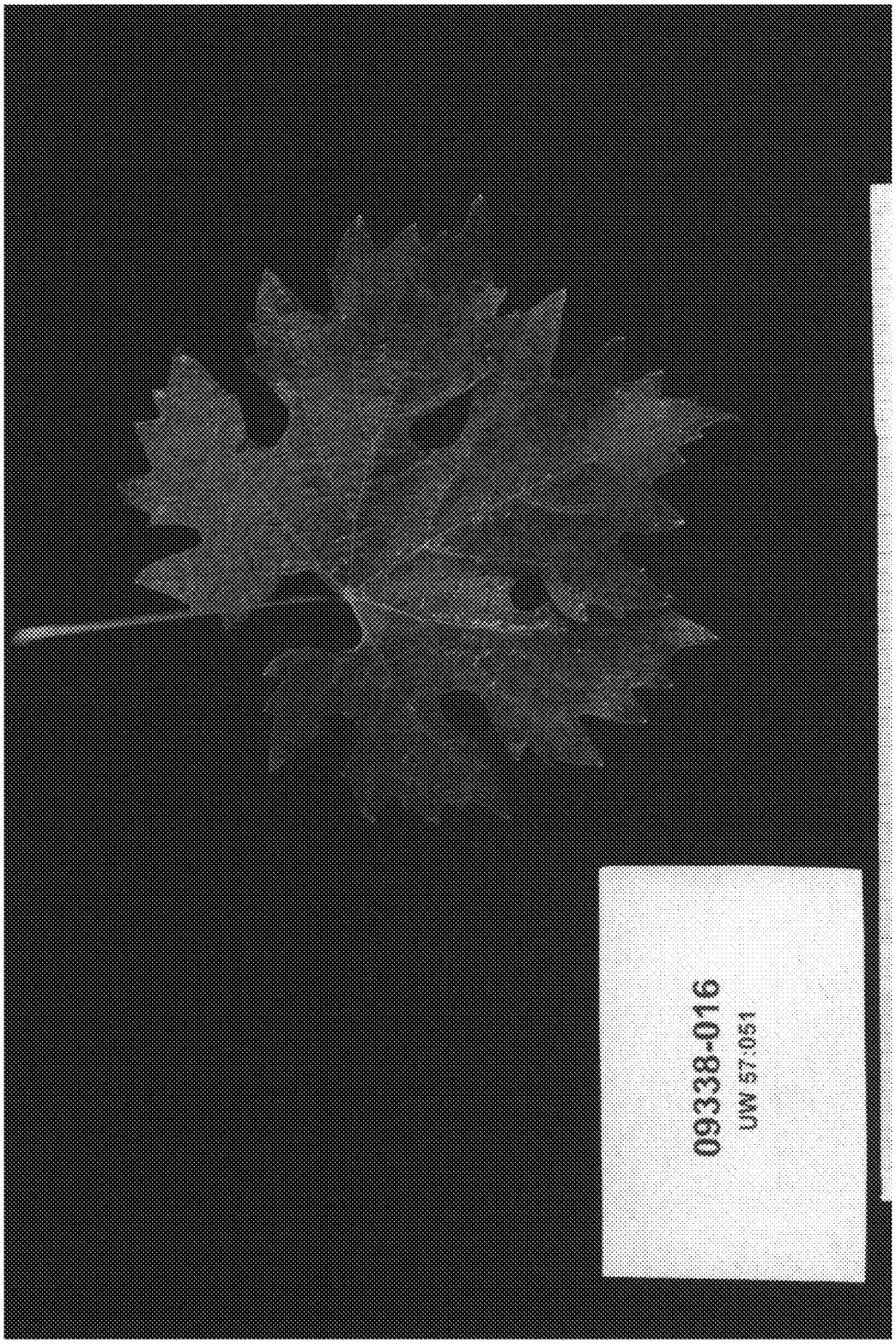
FIG. 2 illustrates the upper surface of a leaf of grapevine plant variety 'Caminante Blanc'.
Figure 3:
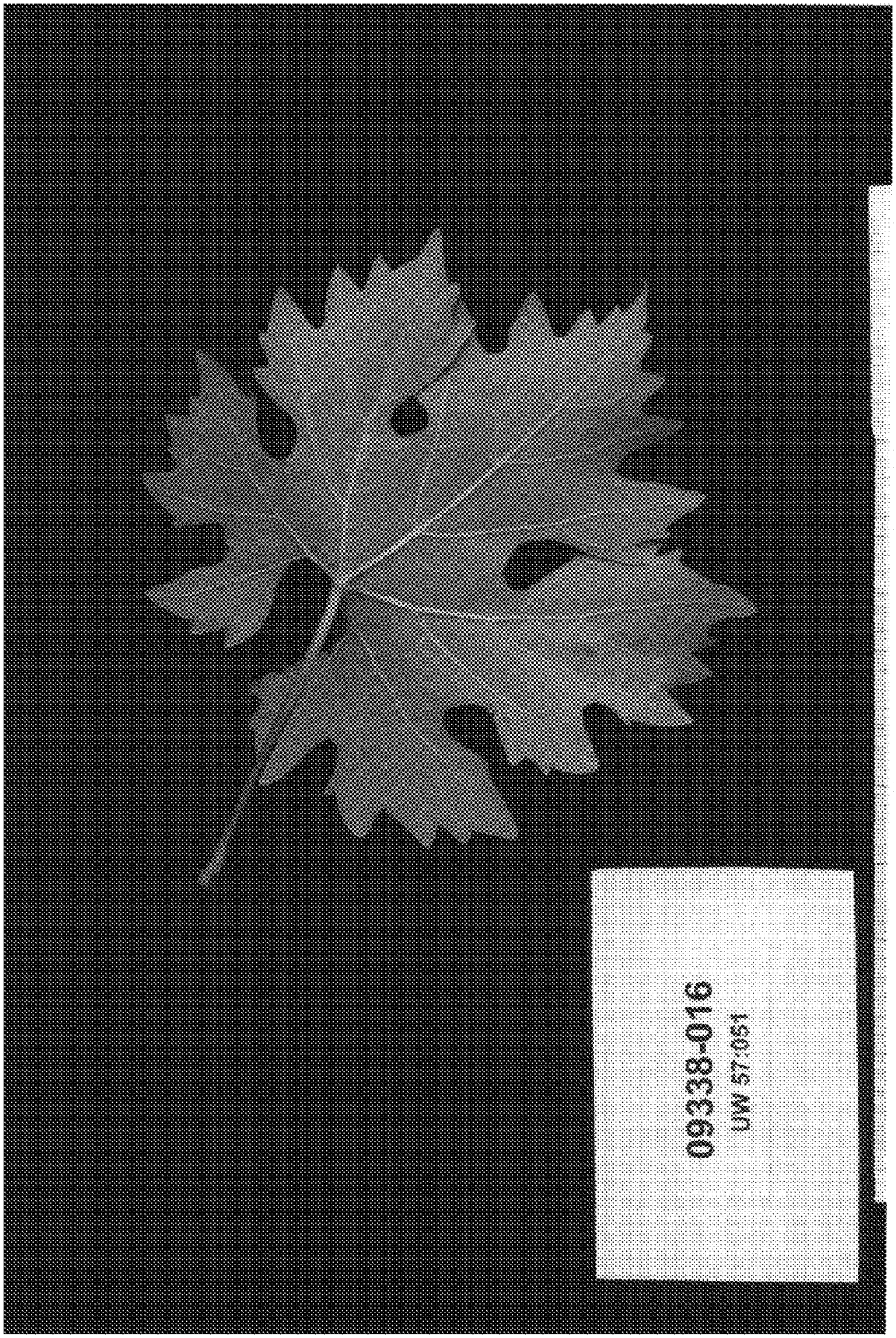
FIG. 3 illustrates the lower surface of a leaf of grapevine plant variety 'Caminante Blanc'.
Figure 4:
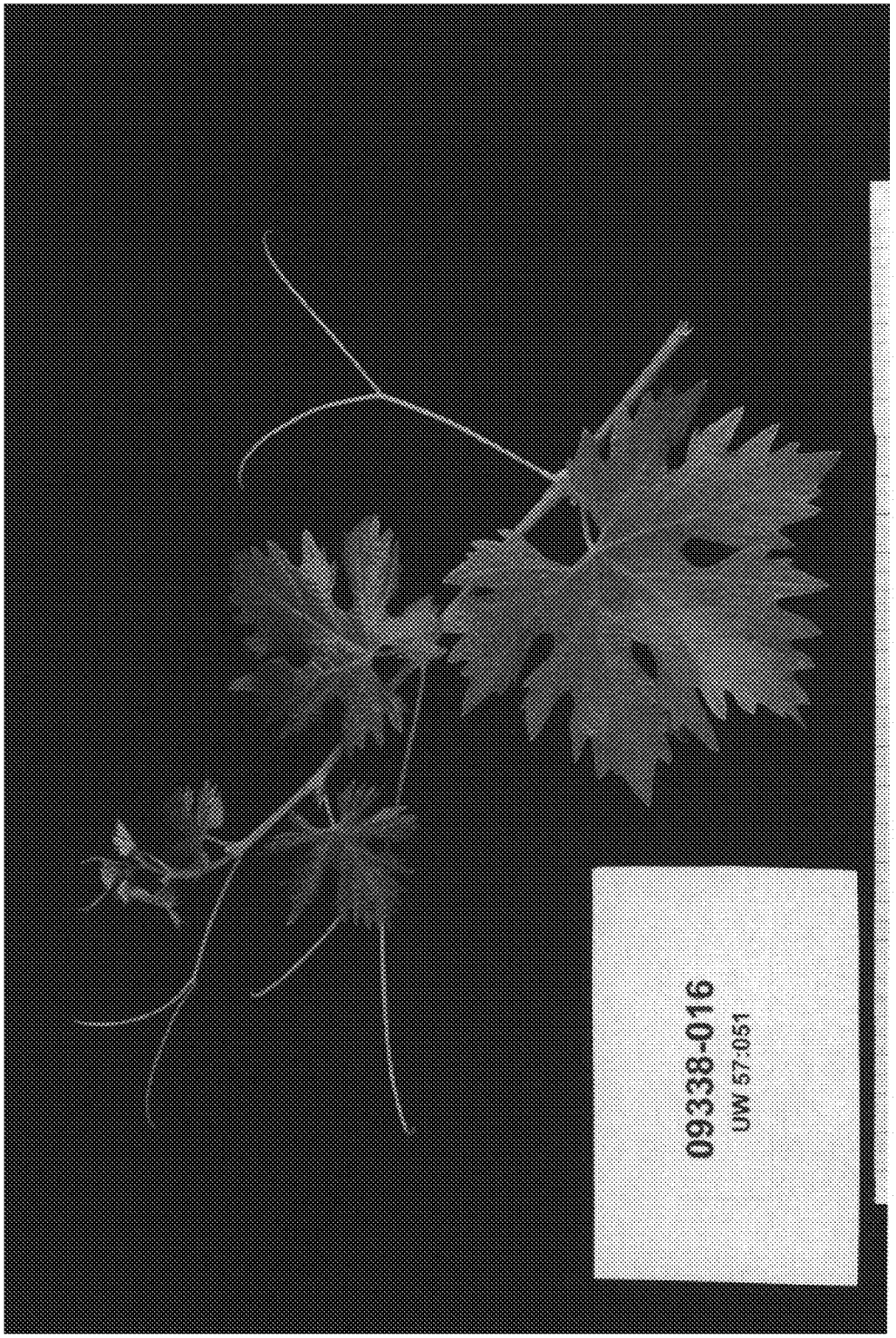
FIG. 4 illustrates a section of a shoot tip of grapevine plant variety 'Caminante Blanc'.
Figure 5:
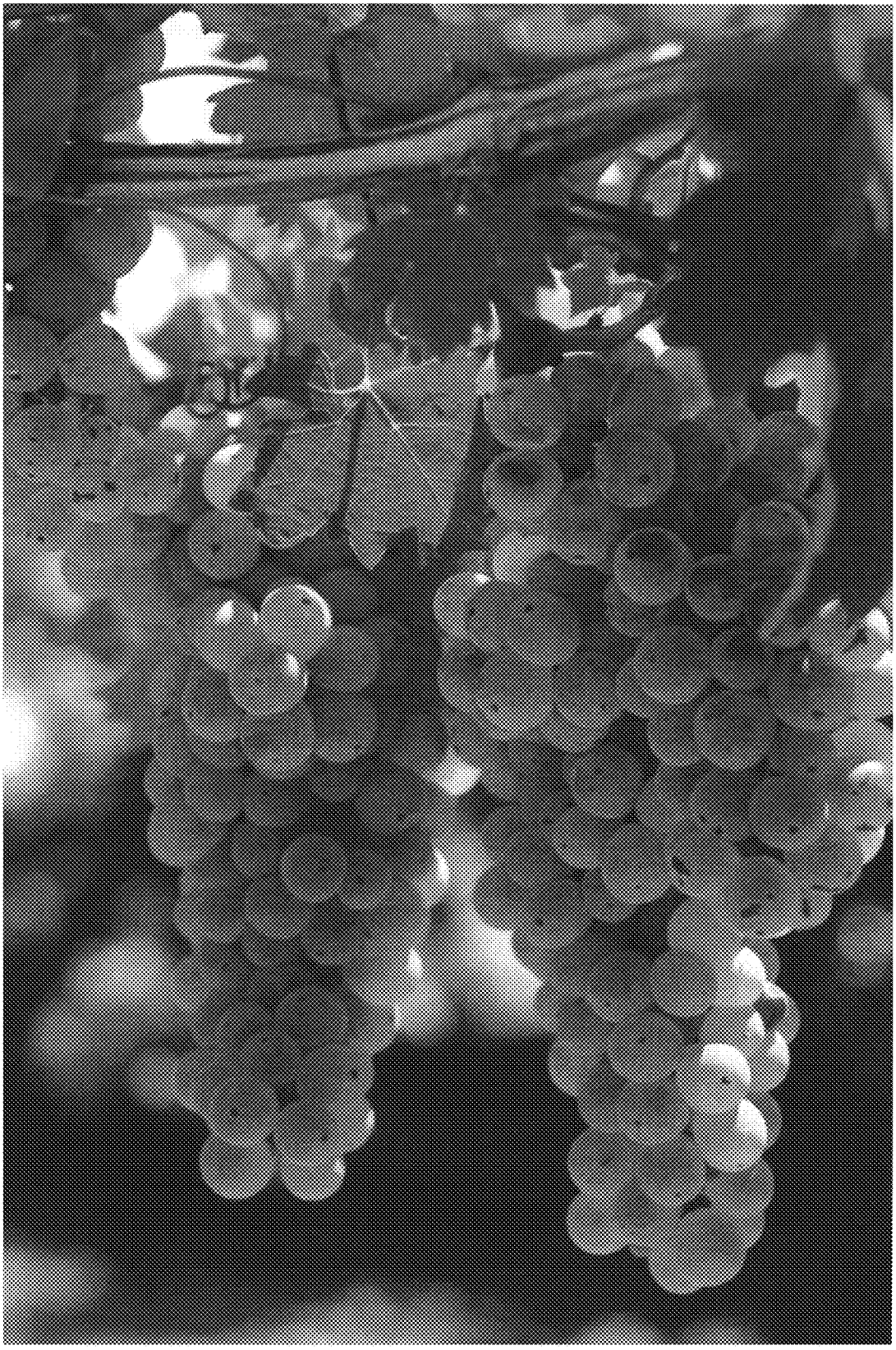
FIG. 5 illustrates a plant of grapevine plant variety 'Caminante Blanc' bearing clusters of berries.
Figure 6:
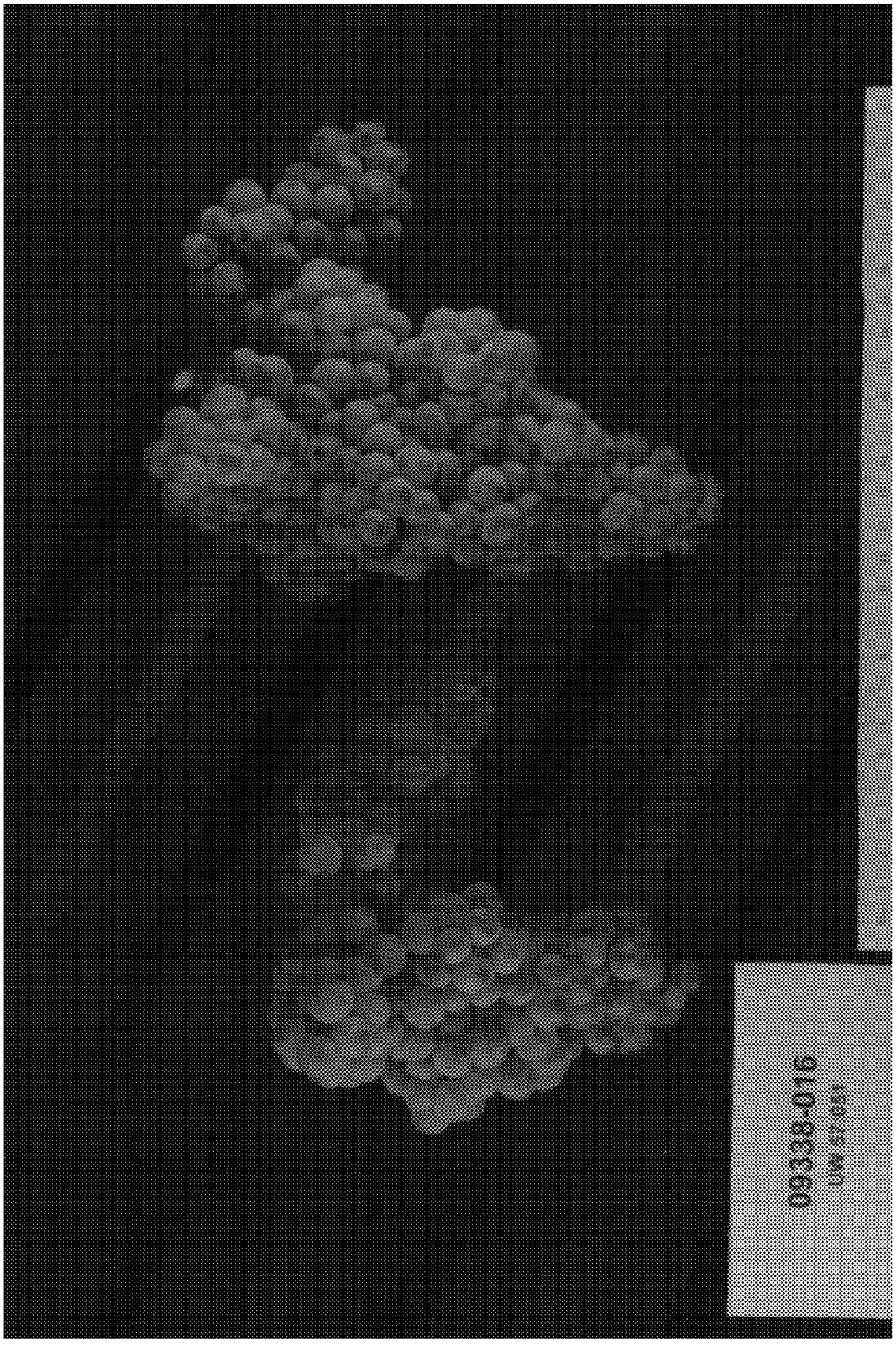
FIG. 6 illustrates a cluster of grapes of grapevine plant variety 'Caminante Blanc'.

'Caminante Blanc' has far better PD resistance and wine quality when compared with 'Blanc du Bois' and 'Lenoir'. In other words, 'Caminante Blanc' combines very strong resistance to *X. fastidiosa* with the wine quality of internationally acclaimed wine grape cultivars. 'Caminante Blanc' was selected as a variety that exhibits high resistance to *X. fastidiosa* and *V. vinifera*-like wine quality. The data presented below are intended to further characterize 'Caminante Blanc'. The appearance of 'Caminante Blanc' is illustrated in FIGS. 2-5, and further characteristics of 'Caminante Blanc' are shown in FIG. 1 and Tables 1-5.

FIG. 1 presents the DNA fingerprinting profile for 'Caminante Blanc' and nine pure *Vitis vinifera* cultivars for comparison with the standard set of internationally agreed-upon genetic markers. This SSR fingerprinting profile can be used for DNA-based identification.

Table 1 presents typical phenological data for 'Caminante Blanc' grown in the UC Davis vineyards. These data are for 2016, but the ranking of the selections in regard to an early cultivar ('Pinot Noir') and a late cultivar ('Cabernet Sauvignon') have been typical over years. In general, 'Caminante Blanc' is phenologically mid-season. Based upon the percentage of *V. vinifera* in the present variety and the data regarding its parents, the variety is expected to grow in USDA Hardiness Zone 6-7. It is not expected to be drought tolerant

TABLE 1

Average phenological states for 'Caminante Blanc'. 'Cabernet Sauvignon' (late) and 'Pinot noir' (early) are included as comparisons. All data were taken from vineyards.

| Cultivar | Budbreak | 50% bloom | 50% veraison | 24 °Brix |
|---|---|---|---|---|
| 'Caminante Blanc' | 3/17 | 5/6 | 7/20 | 8/17 |
| 'Cabernet Sauvignon' | 3/24 | 5/7 | 7/21 | 8/30 |
| 'Pinot Noir' | 3/10 | 4/30 | 7/9 | 8/9 |

Table 2 presents the average cluster and berry data for 'Caminante Blanc', and averaged over multiple years.

TABLE 2

Average cluster and berry sizes of 'Caminante Blanc' and its comparison varieties. Data are averages over multiple years.

| Genotype | Number of Years | Avg. Cluster Wt. (g) | t-test Cluster Wt. | Avg. Wt. (g) | t-test Berry Wt. | Berry Clusters |
|---|---|---|---|---|---|---|
| 'Caminante Blanc' | 5 | 290 | ab | 1.2 | c | Compact |
| 'Blanc du Bois' | 6 | 148 | d | 1.5 | a | Well-filled |
| 'Cabernet Sauvignon' | 6 | 132 | d | 1.2 | c | Loose to well-filled |
| 'Chardonnay' | 6 | 196 | cd | 1.5 | ab | Well-filled to compact |
| 'Lenoir' | 6 | 157 | d | 1.3 | bc | Loose |

Table 3 presents the average yield per vine data taken over 2016 to 2018.

TABLE 3

Average production data for 'Caminante Blanc' and its comparison varieties. Data are averages from three years (2016 to 2018).

| Genotype | Avg. Yield/ Vine (kg) | Std. Dev. (kg) | t-test | Number of Years |
|---|---|---|---|---|
| 'Caminante Blanc' | 7.3 | 0.9 | a | 3 |
| 'Blanc du Bois' | 12.7 | 1.8 | a | 3 |
| 'Cabernet Sauvignon' | 10.9 | 1.8 | a | 3 |
| 'Chardonnay' | 10.9 | 3.2 | a | 3 |
| 'Lenoir' | 20.0 | 6.8 | b | 3 |

Mean berry juice data were also taken and Table 4 presents this data over a five-year period between 2014 and 2018. These values are consistent with cultivars that produce high quality wines.

TABLE 4

Average juice data for 'Caminante Blanc' and its comparison varieties. Data are averages from five years (2014 to 2018).

| Genotype | Avg. °Brix | t-test Avg. °Brix | Avg. pH | t-test Avg. pH | Avg. titratable acidity (g/L) | t-test Avg. TA | Avg. L-malic acid (g/L) | t-test Avg. MA |
|---|---|---|---|---|---|---|---|---|
| 'Caminante Blanc' | 22.2 | de | 3.55 | bc | 5.8 | cd | 1.9 | bcd |
| 'Blanc du Bois' | 23.5 | c | 3.58 | bc | 5.2 | de | 2.3 | bcd |
| 'Cabernet Sauvignon' | 25.8 | b | 3.74 | abc | 5.2 | de | 1.9 | bcd |
| 'Chardonnay' | 23.3 | cd | 3.68 | bc | 5.9 | cd | 2.4 | bc |
| 'Lenoir' | 21.3 | e | 3.96 | a | 9.1 | a | 4.5 | a |

*Xylella fastidiosa* susceptibility data are presented in Table 5, which presents the levels of *X. fastidiosa* in relationship to tolerant ('Blanc du Bois' and to a lesser extent, 'Lenoir') and susceptible ('Chardonnay' and 'Cabernet Sauvignon') cultivars. These are also mean data from repeated testing over seasons and greenhouses. Because of the high variation in greenhouse conditions, at least four standards (bio-controls) were always used: 'b43-17', 'Blanc du Bois', 'Lenoir', and 'Chardonnay' (and occasionally other *V. vinifera* cultivars), which allows the data to be compared across greenhouses, tests and seasons. None of these varieties are patented. These varieties tend to be very consistent in the amounts of bacteria they support as well as the severity of their disease expression. The cut-off between resistant and susceptible is usually between 75,000 and 250,000 colony forming units per milliliter (cfu/ml).

TABLE 5

*Xylella fastidiosa* concentrations based on ELISA readings and converted to colony forming units (cfu/ml). *Vitis arizonica* 'b43-17' is the source of resistance in the breeding program.

| Cultivar | Geometric Mean cfu/ml | t-test | Least Sq. Mean | Std. Error | Number of Times Tested |
|---|---|---|---|---|---|
| 'b43-17' | 12423 | a | 9.4 | 0.2 | 11 |
| 'Caminante Blanc' | 126965 | b | 11.8 | 0.4 | 4 |
| 'Blanc du Bois' | 859096 | c | 13.7 | 0.2 | 11 |
| 'Lenoir' | 2421748 | d | 14.7 | 0.6 | 2 |
| 'Chardonnay' | 5197228 | d | 15.5 | 0.2 | 11 |
| 'Cabernet Sauvignon' | 6582993 | d | 15.7 | 0.8 | 1 |

TABLE 6 shows phenotype of 'Caminante Blanc'. The variety has normal hermaphroditic flowers and typical floral development as is found in commercial *V. vinifera* wine grapes.

| | 'Caminante Blanc' |
|---|---|
| Berry size (L, W) | 1.3 × 1.4 cm |
| Berry weight, shape | 0.8 g/round |
| Seed number, length and width typical for *V. vinifera* wine grapes, but not measured | 2 |
| Cluster #, L, W, shape, compactness, 2 clusters/shoot | 4.0 × 7.0 cm, short compact narrow conical, winged to double |
| Yield kg | 11.5 |
| Pruning weights | 1.55 kg |
| Trunk width at 30 cm | 3.0 cm |
| Trunk color and texture | Rough shaggy bark 178D |
| Woody shoots diameter above cluster/ and internode length | 0.8 cm/6.6 cm |
| Woody shoot texture and color | First year bark adheres but peels in strips in second year 164B |
| Active shoot color, internode color above the cluster zone/ cluster zone shoot diameter/internode length (shoots same size as woody canes in the cluster zone) | 144C 145A 0.8/6.6 cm |
| Tendril length, diameter | 15.0 0.2 |
| Tendril color, | N144D |
| Opposite leaves and alternating 2 nodes skip 2 nodes skip | |
| Seed color | 165B |
| Cluster size L, W | 4.0 × 7.0 cm |
| #Berries/cluster | 332 |
| Berry color skin and waxy bloom | 145A 190D |
| Berry flesh color | 145A |
| Leaves L, W | 19.0 × 19.0 cm |
| Leaf arrangement, shape, and color Top/Bottom | Alternate, palmate with 5 lobes 141A/144B |

TABLE 6-continued shows phenotype of 'Caminante Blanc'. The variety has normal hermaphroditic flowers and typical floral development as is found in commercial *V. vinifera* wine grapes.

| | 'Caminante Blanc' |
|---|---|
| Petiole L, diameter, texture | 10.7 0.4 smooth |
| Petiole color | 71A |
| Shoot tip color (first opened leaf) | 79A/143A |
| Budbreak | Mar. 17 |
| Bloom date | May 12 |
| Harvest date | Aug. 18 |
| Peduncle L, diam., color, texture | 1.0 0.5 N144B Smooth |

Flower Descriptions

The floral buds and flower clusters are formed with in the latent (dormant) bud in the year before flowering. As the pre-formed nodes on the compressed stems within the latent bud expand and the flower clusters begin developing and the individual flowers on the panicle begin forming. They are very small 2-4 mm and closer to 2 mm with wine grapes.

Berry Descriptions

The variety is not a "slip-skin" type grape. They have skin that adheres to the flesh tightly. They are not firm at ripeness and are soft compared to modern era table grapes at harvest. The pedicels have normal attachment to the berries and are not distinguishable from other *V. vinifera* wine grapes in this or other morphological features, nor in juice and wine analysis.

Fruit and Juice Parameters

YAN is yeast assimilable nitrogen and helps predict fermentation success. The white grapes have no tannin or anthocyanin values. Seed color is rated as green to brown for mature seeds.

Leaf Descriptions

Rounded leaves with lateral lobes with deep sinuses, and sinuses cutting into the lateral lobes, lyre-U shaped petiolar sinus, large irregular teeth, light tomentum on the adaxial leaf surface, red (71A) petioles with color that diffuses into the main veins

Berry Descriptions

The variety is not a "slip-skin" type grape. They have skin that adheres to the flesh tightly. They are not firm at ripeness and are soft compared to modern era table grapes at harvest. The pedicels have normal attachment to the berries and are not distinguishable from other *V. vinifera* wine grapes in this or other morphological features, nor in juice and wine analysis.

Fruit and Juice Parameters for the 5 Releases

YAN is yeast assimilable nitrogen and helps predict fermentation success. The white grapes have no tannin or anthocyanin values. Seed color is rated as green to brown for mature seeds.

TABLE 7

| presents the wine characteristics of 'Caminante Blanc' | | | | | | |
|---|---|---|---|---|---|---|
| | °Brix | TA (g/L) | pH | L-malic acid (g/L) | Potassium (mg/L ) | YAN (mg/L, as N) |
| 'Caminante Blanc' | 21.3 | 5.7 | 3.50 | 1.3 | 1660 | 226 |

| Table 8 presents the juice, fruit and seed phenotype of 'Caminante Blanc' | | | | |
|---|---|---|---|---|
| | Juice Hue | Juice Intensity | Juice Flavor | Skin Flavor |
| 'Caminante Blanc' | green | Lt light | green apple | grass, veg, astringent |

-continued

| Table 8 presents the juice, fruit and seed phenotype of 'Caminante Blanc' | | | | |
|---|---|---|---|---|
| | Skin Tannin (1 = low, 4 = high) | Seed Color (1 = gr, 4 = br) | Seed Flavor | Seed Tannin (1 = high, 4 = low) |
| 'Caminante Blanc' | 3 | 4 | spicy, hot, sl bitter | 2 |

'Caminante Blanc' has excellent PD resistance. However, itis highly susceptible to a wide range of pests and diseases in a manner similar to other *V. vinifera* cultivars, and thus it must be treated as a pure *V. vinifera* cultivar are treated in terms of susceptibility to fungal diseases and pests. 'Caminante Blanc' has no known tolerance to adverse weather.

What is claimed is:

1. A new and distinct variety of grapevine plant designated 'Caminante Blanc' as shown and described herein.

* * * * *

| Marker Alleles for the International Set of SSR Loci for Fingerprinting Grape | | | | | | | | | | | | | | | | | | | | |
|---|---|---|---|---|---|---|---|---|---|---|---|---|---|---|---|---|---|---|---|---|
| Cultivar | VVMD5 | | VVMD7 | | VVS2 | | VrZAG79 | | VrZAG62 | | VVMD31 | | VVMD27 | | VVMD32 | | VVIP26 | | CH14-77 | |
| Caminante Blanc | 226 | 235 | 235 | 235 | 132 | 146 | 238 | 242 | 184 | 192 | 206 | 210 | 175 | 183 | 237 | 237 | 146 | 160 | 178 | 202 |
| Riesling | 226 | 235 | 235 | 235 | 134 | 146 | 242 | 242 | 184 | 190 | 202 | 206 | 169 | 183 | 237 | 237 | 160 | 166 | 178 | 178 |
| Alicante Bouschet | 220 | 233 | 235 | 239 | 128 | 140 | 238 | 252 | 184 | 184 | 208 | 208 | 175 | 188 | 247 | 269 | 154 | 160 | 178 | 178 |
| Chenin blanc | 220 | 226 | 235 | 249 | 128 | 128 | 240 | 246 | 192 | 196 | 212 | 212 | 183 | 185 | | | 160 | 160 | 178 | 185 |
| Zinfandel | 220 | 230 | 243 | 245 | 128 | 138 | 232 | 254 | 196 | 200 | 208 | 210 | 173 | 175 | 253 | 261 | 160 | 160 | 178 | 178 |
| Touriga Nacional | 220 | 220 | 235 | 235 | 138 | 146 | 240 | 240 | 184 | 190 | 200 | 212 | 175 | 183 | 237 | 269 | 140 | 154 | 168 | 178 |
| Semillon | 233 | 235 | 235 | 245 | 132 | 138 | 234 | 238 | 190 | 200 | 210 | 212 | 175 | 179 | 237 | 247 | 154 | 160 | 178 | 178 |
| Palomino | 220 | 220 | 239 | 243 | 128 | 128 | 250 | 254 | | | 200 | 212 | 173 | 175 | 253 | 259 | 154 | 160 | 178 | 178 |
| Chardonnay | 229 | 233 | 235 | 239 | 132 | 138 | 238 | 240 | 184 | 192 | 210 | 212 | 175 | 183 | 237 | 269 | 154 | 180 | 178 | 178 |
| Cabernet Sauvignon | 226 | 235 | 235 | 235 | 134 | 146 | 242 | 242 | 184 | 190 | 202 | 206 | 169 | 183 | 237 | 237 | 160 | 166 | 178 | 178 |

FIG. 1